United States Patent [19]
Whitten et al.

[11] Patent Number: 5,710,324
[45] Date of Patent: Jan. 20, 1998

[54] INHIBITORS OF NITRIC OXIDE BIOSYNTHESIS

[75] Inventors: Jeffrey P. Whitten, Cincinnati; Ian A. McDonald, Loveland; Laurie E. Lambert, Morrow, all of Ohio; Niall S. Doherty, Lyme, Conn.

[73] Assignee: Merrell Pharmaceuticals Inc., Cincinnati, Ohio

[21] Appl. No.: 317,458

[22] Filed: Oct. 4, 1994

Related U.S. Application Data

[60] Continuation of Ser. No. 201,915, Feb. 25, 1994, abandoned, which is a division of Ser. No. 91,082, Jul. 13, 1993, Pat. No. 5,318,992, which is a continuation of Ser. No. 840,572, Feb. 24, 1992, abandoned, which is a continuation of Ser. No. 585,349, Sep. 19, 1990, abandoned, which is a continuation-in-part of Ser. No. 485,109, Feb. 26, 1990, abandoned.

[51] Int. Cl.$^6$ .......................... A61K 31/195; C07C 61/04
[52] U.S. Cl. .......................... 562/506; 562/439; 562/440; 562/502; 560/124; 560/168; 514/565; 514/551; 514/921
[58] Field of Search .......................... 562/502, 506, 562/439, 440; 514/565, 551, 921; 560/124, 168

[56] References Cited

U.S. PATENT DOCUMENTS

| | | | |
|---|---|---|---|
| 4,686,283 | 8/1987 | Nestor et al. | 530/327 |
| 4,686,286 | 8/1987 | Nestor et al. | |
| 5,028,627 | 7/1991 | Kilbourn et al. | |

FOREIGN PATENT DOCUMENTS

| | | |
|---|---|---|
| 0196841 | 3/1986 | European Pat. Off. |
| 0230037 | 12/1986 | European Pat. Off. |
| 0277561 | 1/1988 | European Pat. Off. |
| 9104023 | 4/1991 | WIPO |

OTHER PUBLICATIONS

P. K. Moore et al., Br. J. Pharmacol. 99, 408–412 (1990).
John J. Nestor, Jr. et al., J. Med. Chem 31, 65–72 (1988).
Aisaka, K. et al., *Biochemical and Biophysical Research Communication*, vol. 160, No. 2, pp. 881–886, 1990.
Fukuto, Jon M., et al., *Biochemical and Biophysical Research Communication* vol. 168, No. 2, pp. 458–465 (1990).
Abstract #1513 From American Society for Biochemistry and Molecular Biology The American Association of Immunologists, Moint Meeting, New Orleans, LA (1990).
Stevens, Charles F., *Nature* vol. 336, pp. 308–309 (1988).
Stuehr, Dennis J., et al., J. Exp. Med. vol. 169, pp. 1011–1020 (1989).
Kaplan, S. S., et al., *Blood*, vol. 74, No. 6, pp. 1885–1887 (1989).
*Trends in Pharmacological Sciences* vol. 10, No. 11, pp. 427–431 (1989).
Garthwaite, J. et al., *Nature* vol. 336, pp. 385–388 (1988).
Bredt, D. S. et al., Proc. Natl. Acad. Sci, USA, vol. 86, pp. 9030–9033 (1989).
Moncada, S. et al.,*Biochemical Pharmacology*, vol. 38, No. 11, pp. 1709–1715 (1989).
Chemical Abstracts, vol. 84, (1976) p. 20, Abstracts No. 197d.
Chemical Abstracts vol. No. 83 (Jul.–Dec., 1975), Abstracts No. 206526y.
Tetrahedron Letters, vol. 29, No. 47, pp. 6183–6184, 1988.
Chemical Abstracts, vol. No. 84, (1976) p. 194, Abstracts No. 197d.
Biochemical Pharmacology, vol. 38, No. 11, pp. 1709–1715, 1989; Biosynthesis of Nitric Oxide from L–Arginine, Moncada et al.
Chemical Abstracts AN 1992: 470338 (Nestor et al. corresponding to EP 472220) Aug. 24, 1990.

*Primary Examiner*—Raymond Henley, III
*Assistant Examiner*—Keith MacMillan
*Attorney, Agent, or Firm*—Ruth E. Homan

[57] ABSTRACT

The present invention is directed to a new class of compound which are useful as inhibitors of the biosynthesis of nitric oxide.

13 Claims, No Drawings

INHIBITORS OF NITRIC OXIDE BIOSYNTHESIS

CROSS-REFERENCE TO RELATED APPLICATION

This is a continuation of application Ser. No. 08/201,915, filed Feb. 25, 1994, now abandoned which is a division of application Ser. No. 08/091,082, filed Jul. 13, 1993 allowed Dec. 7, 1993 U.S. Pat. No. 5,318,992 which is a continuation of application Ser. No. 07/840,572 filed Feb. 24, 1992 now abandoned; which is a continuation of application Ser. No. 07/585,349 filed Sep. 19, 1990, now abandoned which is a continuation in part of application Ser. No. 07/485,109 filed Feb. 26, 1990 now abandoned which is herein incorporated by reference.

The present invention is directed to a new class of arginine derivatives which are useful in inhibiting the biosynthesis of nitric oxide from L-arginine. Another aspect of this invention is directed to the treatment of a number of disease states such as, for example, conditions associated with low blood pressure and to the treatment of inflammatory diseases and stroke. A further aspect of the invention is directed to compositions containing these arginine derivatives.

BACKGROUND OF THE INVENTION

It has recently been discovered that nitric oxide mediates a number of physiological processes. It serves as a signal transduction mechanism in the central nervous system, is intimately involved with the regulation of blood pressure, and is produced by activated inflammatory cells thereby playing a role in pathological inflammatory conditions.

Garthwaite et al. and Stevens reported that stimulation of the glutamate site of the NMDA receptor complex leads to the release of nitric oxide. The nitric oxide stimulates the guanylate cyclase present in the CNS which in turns leads to an increase in cyclic GMP levels. A great deal of attention has been focused upon these excitatory amino acid receptors because it is believed that they are associated with learning and development. It is also believed that over-stimulation of these receptors is associated with a number of disease states such as, for example, epilepsy, stroke, and neurodegenerative diseases such as senile dementia, etc. *Nature*, 336, pages 308–309 and 385–388 (November 1988).

Knowles et al. reported the mechanism by which the nitric oxide is formed. An enzymatic reaction occurs in which L-arginine is converted into nitric oxide and citrulline. Knowles et al. also reported that the presence of N-monomethyl-L-arginine inhibited this enzymatic transformation. *Proc. Natl. Acad Sci. USA*, 86, pages 5159–5161 (July 1989).

Moncada et al. provided a review of the information which had been published to date regarding the physiological role of nitric oxide. Moncada et al. described the work of Knowles and Garthwaite regarding the role of nitric oxide in the CNS and postulated that nitric oxide is involved in seizures and other disease states associated with excessive excitatory neurotransmission. *Biochemical Pharmacology*, 38, No. 11, pages 1709–1715, (1989).

Moncada et al. reported that nitric oxide is associated with the regulation of blood pressure. These authors reported that an enzymatic pathway exists in the vasculature by which L-arginine is converted into nitric oxide. *Nature*, 333, pages 664–666 (1988). The nitric oxide relaxes the smooth muscles of the vasculature, producing dilation of these vessels which results in a lowering of blood pressure. Inhibition of nitric oxide synthesis by the administration of N-monomethyl-L-arginine produces a marked rise in blood pressure in test animals. *Proc. Natl. Acad. Sci, USA*, 86, pages 3375–3378 (1989).

Moncada et al. also reviewed earlier literature which reported that nitric oxide can be produced in large amounts by macrophages and polymorphonuclear leucocytes (PMN) and is associated with the effector functions of the cells. N-monomethyl-L-arginine inhibits the synthesis of nitric oxide by these cells.

The discovery of compounds capable of inhibiting the biosynthesis of nitric oxide would provide a new treatment for a number of disease states. They could be utilized in the treatment of conditions associated with low blood pressure such as, for example, shock. They could also be used to treat conditions caused by over-activity of the NMDA receptor complex such as epilepsy, stroke, neurodegenerative diseases, etc. They could also be used to treat conditions associated with excessive production of nitric oxide by macrophages and polymorphonuclear leucocytes such as arthritis, cirrhosis, transplant rejections, etc.

DETAILED DESCRIPTION OF THE INVENTION

In accordance with the present invention it has been discovered that the biosynthesis of nitric oxide can be inhibited by the following class of arginine derivatives:

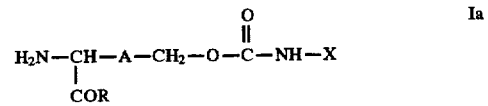

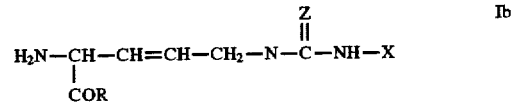

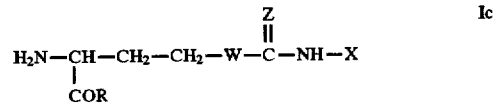

in which:

a) in Formula Ia, A is represented by —$(CH_2)_2$—, —$(CH_2)_3$— or —CH=CH—; X is represented by cyano, cyclopropyl, 2-propyne, 2,3-butadiene or $NHR_2$ in which $R_2$ is represented by H, —$CF_3$, —$CH_2CF_3$, or $C_{1-6}$ alkyl; and R is represented by an amino acid or OM, in which M is represented by H, $C_{1-6}$ alkyl, benzyl, phenyl, pivoyl methyl ether, and the pharmaceutically acceptable salts thereof;

b) in Formula Ib, R and X are as defined as above, Z is represented by 0 or $NR_1$ in which $R_1$ is represented by H, —$CF_3$, —$CH_2CF_3$, or $C_{1-6}$ alkyl; and the pharmaceutically acceptable salts thereof and;

c) in Formula Ic, W is represented by a substituent selected from the group consisting of —$CH_2$—NH—, —$(CH_2)_2$—NH—, —$CH_2$—NH—NH—, —$CH_2$—O—NH—, —NH—NH—, and —O—NH—; and R, Z, and X are as defined above; and the pharmaceutically acceptable salts thereof; with the following proviso's:

1) that when W is —NH—NH or —$CH_2$—NH—NH— then Z must be represented by O;

2) when Z is represented by O and X is represented by $NR_1$, then W must be —$CH_2$—NH or —$(CH_2)_2$—NH— and;

3) that when W is represented by $CH_2$—NH, Z is represented NH, and X is $NHR_2$, then $R_2$ is not represented by H.

The compounds encompassed by Formulae Ia–c inhibit the biosynthesis of nitric oxide. They prevent the bioconversion of L-arginine into nitric oxide and citrulline. Thus these compounds will be useful in the treatment of a number of disease states in which excessive levels of nitric oxide is implicated.

As used in this application: the term, a) "cyano" refers to the following substituent: —CN;

b) "cyclopropyl" refers to the following substituent:

c) "2-propyne" refers to the following substituent: $CH_2$—C≡CH;

d) "2,3-butadiene" refers to the following substituent: —$CH_2$—CH=C=$CH_2$;

e) "$C_{1-6}$ alkyl" refers to a straight chain, branched, or cyclic alkyl group containing up to 6 carbon atoms. Representative examples of suitable alkyl groups include, methyl, ethyl, propyl, isopropyl, n-butyl, t-butyl, pentyl, hexyl, cyclopropyl, and cyclopentyl;

f) "pivoyl methyl ether" refers to the following substituent: —$CH_2$—O—CO—C—$(CH_3)_3$;

g) "amino acid" refers to one of the naturally occurring amino acids, and more preferably either aspartic acid or glutamic acid. The amino acids encompassed by the present invention are listed below in Table I. It is preferred that these amino acids be in their L-configuration. Their structures are disclosed in the well known text Lehninger's Biochemistry. The amine function of these amino acids is bonded to the carbonyl group adjacent to R in the compounds of Formula Ia–c.

TABLE I

| AMINO ACID | SYMBOL |
| --- | --- |
| Alanine | Ala |
| Arginine | Arg |
| Aspargine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

Since the compounds of Formula I are derivatives of the amino acid arginine, they can exist as acid addition salts, basic addition salts, as zwitterions, or as their free base. Thus the term "pharmaceutically acceptable salts" should be construed as encompassing pharmaceutically acceptable acid additions salts, pharmaceutically acceptable basic addition salts or the zwitterion form of the molecule.

The expression "pharmaceutically acceptable acid addition salts" is intended to apply to any non-toxic organic or inorganic acid addition salt of the base compounds represented by Formula Ia–c or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form.

The expression "pharmaceutically acceptable basic addition salts" is intended to apply to any non-toxic organic or inorganic basic addition salts of the compounds represented by Formula Ia–c or any of its intermediates. Illustrative bases which form suitable salts include alkali metal or alkaline-earth metal hydroxides such as sodium, potassium, calcium, magnesium, or barium hydroxides; ammonia, and aliphatic, allcyclic, or aromatic organic amines such as methylamine, dimethylamine, trimethylamine, and picoline.

All of the compounds of Formula Ia–c exist as optical isomers. Those compounds of Formula Ia–c in which X is represented by a butadiene will exist as stereoisomers as well. Those compounds of Formula Ia–c which are in the L-configuration are preferred due to their superior potency. However, any reference to the compounds of Formula Ia–c or to any of their intermediates should be construed as referring to either an optical isomer, an enantiomer, or to a racemic mixture. The specific optical isomers and enantiomers can be separated and recovered by techniques known in the art such as chromatography on chiral stationary phases or resolution via chiral salt formation and subsequent separation by selective crystallization. Alternatively utilization of a specific optical isomer or enantiomer as the starting material will produce the corresponding isomer or enantiomer as the final product.

Those compounds of Formula Ia, in which A is represented by an ethlylene moiety, and all of the compounds of Formula Ib will exist as geometrical isomers. Any reference to the compounds of Formula Ia or Ib should be construed as encompassing either the cis or trans isomers.

Those compound of Formula Ib in which Z is represented by $NR_2$, as well as those compounds of Formula Ic in which Z is $NR_2$ while W is —$CH_2$—NH or —$(CH_2)_2$—NH— will exist as tautomers. The geminal nitrogen atoms will exist in a state of equilibrium in which they share a pair of electrons. Any reference to the compounds of Formula Ib or Ic should be construed as encompassing any of these tautomers.

Examples of compounds encompassed by Formula Ia–c include:

1) 2-amino-5-[(hydrazinoiminomethyl)amino]-3-pentenoic acid
2) $N^5$-[Imino-(cyclopropylamino)-iminoethyl]-L-Ornithine
3) $N^5$-[Imino-(2-propynyl)-amino)methyl]-L-ornithine
4) 5-(Hydrazinoiminomethy)-norvaline
5) 2-amino-5-[[Imino-(2-propynylamino)methyl]amino]-3-pentenoic acid
6) 2-Amino-5-[(hydrazinocarbonyl)amino]-3-pentenoic acid
7) $N^5$-(Hydrazinocarbonyl)-L-ornithine
8) O-[Hydrazino-carbonly]-homoserine
9) 2-Amino-5-[(hydrazinocarbonyl)amino]-3-pentenoic acid
10) N-[3,4-Didehydro-$N^5$-(hydrazinoiminomethyl)-L-ornithyl]-L-aspartic acid 11) N-[3,5-Didehydro-$N^5$-(hydrazinoiminomethyl)-L-ornithyl]-L-Glutamic acid
12) N-[$N^5$-[(Cyclopropylamino)iminomethyl]-L-ornithyl]-L-Glutamic acid
13) N-[$N^5$-[(Cyclopropylamino)iminomethyl]-L-ornithyl]-L-aspartic acid
14) N-[$N^5$-Imino-(2-propynylamino)methyl-L-ornithyl]-L-glutamic acid
15) N-[$N^5$-[Imino-(2-propynylamino)methyl]-L-ornithyl]-L-aspartic acid
16) N-[3,4-Didehydro-$N^5$-[imino-(2-propynylamino)methyl]-L-ornithinyl]-L-aspartic acid
17) N-[3,4-Didehydro-$N^5$-[imino-(2-propynylamino)methyl]-L-ornithyl-L-glutamic acid
18) $N^5$-[(Cyclopropylamino)iminomethyl]iminomethyl]-L-ornithine, methyl ester
19) 2-Amino-5-[[imino-(2-propynylamino)methyl]amino]-3-pentenoic acid, methyl ester
20) Hydrazinecarboxylic acid, 4-amino-4-carboxybutyl ester
21) 6-[[(Cyclopropylamino)carbonyl]oxy]-norleucine
22) Hydrazinecarboxylic acid, 4-amino-4-carboxy-2-butenyl ester
23) $N^5$-[Imino(2-methyhydrazino)methyl]-L-ornithine
24) 2-Amino-4-[Z-(hydrazinoiminomethyl)hydrazino]-butanoic acid
25) $N^5$-(Hydrazinoiminomethyl)-L-ornithine
26) O-[(Hydrazinoiminomethyl)-amino]-L-homoersine, flavinate
27) $N^6$-(Hydrazinocarbonyl)-L-lysine
28) 2-Amino-4-[2-[(Cyclopropylamino)carbonyl]hydrazino]-butanoic acid
29) 5-[2-[(Cyclopropylamino)carbonyl]hydrazino]-norvaline It has been discovered that the substituent which is present at the X position can affect the relative activity of the compounds. Those compounds in which X is a bulky substituent such as 2-propyne, cyclopropyl, or 2,3-butadiene show superior activity for inhibiting the production of nitric oxide within the CNS.

The compounds of Formula Ia-c can be made using techniques well known in the art. Those compounds which can be described by Formula Ia can be made using the synthesis outlined below in Reaction Scheme I:

REACTION SCHEME I

STEP A

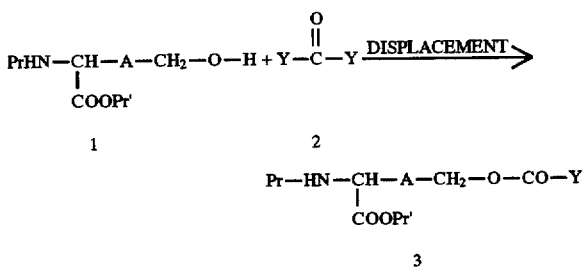

STEP B

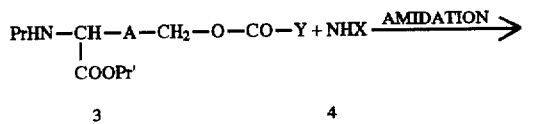

-continued
REACTION SCHEME I

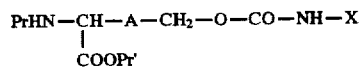

STEP C

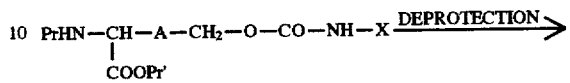

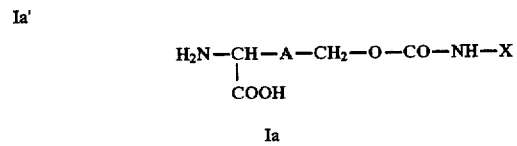

STEP D

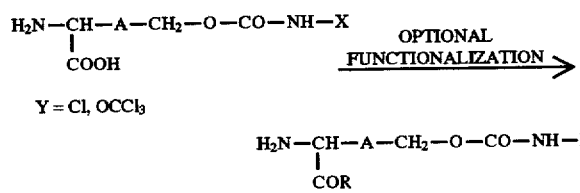

In Step A of Reaction Scheme I, a displacement reaction is carried out between phosgene (2, Y=Cl) or triphosgene (2, Y=OCCl$_3$) and a functionalized amino acid as described by structure (1) in which A is as in Formula I and Pr is a t-butyloxycarbonyl group, while Pr' is a t-butyl group. This displacement reaction produces a chloroformate or a trichloromethylurethane as described by structure (3) in which Pr, Pr' and A are as defined above. In Step B, the chloroformate of structure (3, Y=Cl) or the trichloromethylurethane (3, Y=OCCl$_3$) is subjected to an amidation reaction with an amino-derivative as described by structure (4) in which X is as defined in Formula Ia, thereby producing the protected compound of Formula Ia'. In Step C, the protecting groups Pr and Pr' are removed thus producing a compound of Formula Ia. In Step D, an optional functionalization reaction can be carried out in order to introduce the appropriate R substituent into the molecule at the position indicated.

The displacement reaction of Step A can be carried out using techniques well known in the art. The particular functionalized amino acid of structure (1) which is utilized as a starting material should have the same function at the A position as is desired in the final product of Formula Ia. Typically approximately equivalent amounts of the amino acid of structure (1) and the phosgene or triphosgene are contacted in an organic solvent such as benzene, toluene or methylene dichloride at a temperature range of from about −10° C. to about 60° C. The displacement reaction is typically allowed to proceed for a period of time ranging from about 0.5 to 2 hours.

A molar excess of the amino derivative of structure (4) is then added to the reaction medium in which the displacement was carried out. The amidation reaction of Step B is then allowed to proceed for a period of time ranging from about 0.5 to 8 hours. The amidation reaction is carried out at a temperature range of from about 0°–40° C. Upon completion of the amidation reaction, the desired product can be recovered from the reaction medium by extraction or concentration. It can optionally be purified by flash chromatography as is known in the art. The particular amino-derivative of structure (4) which is utilized as a reactant should have the same substituent at the X position as is desired in the final product of Formula I.

The deprotection reaction of Step C can be carried out using techniques well known in the art. This deprotection reaction produces a compound of Formula Ia in which R is represented by a hydroxyl group as is depicted. The protected compound of Formula Ia' is typically subjected to a mildly acidic hydrolysis with a mineral acid such as hydrochloric acid. The concentration of acid which is utilized is not critical and typically is in the range of from about 1–4M. The deprotection reaction is typically carried out for a period of time ranging from about 0.25–4 hours at a temperature range of from 0°–60° C. The compound of Formula Ia can recovered from the reaction medium by either concentration or extraction as is known in the art. It can then be purified by either ion exchange chromatography or by preparative $C_{18}$ reverse phase chromatography as is known in the art.

If R is to be represented by other than a hydroxyl group, then it is necessary carry out the optional functionalization reaction of Step D. The various ester derivatives of Formula Ia can be prepared utilizing techniques well known in the art. For example if an ester is desired, the deprotected compound of Formula Ia can be contacted with an alcohol corresponding to the desired substituent in the presence of a mineral acid. If R is to be represented by an amino acid, then it can be added to the compounds of Formula I utilizing peptide coupling techniques known in the art. For example, see Meldal et al. Synthesis of a Proposed Antigenic Hexapeptide from *Escheria coli* K88 Protein Fimbriae—*Acta Chem. Scand.*B40: 235–241.

Methods for producing the functionalized amino acids of structure (1) are well known in the art. For example, the preparation of 5-hydroxynorvaline is described in *J. Chem. Soc., Chem. Commun.*, 20, 1583–4 (1987) and the preparation of 6-hydroxynorleucine is described in *Agric. Bio. Chem.*, 42(6), 1275–8 (1979). Methods for producing the amino derivatives of structure (4) are also well known in the art.

The following examples represent typical syntheses of compounds of formula (Ia). These examples are understood to be illustrative only and are not intended to limit the scope of the present invention in any way.

EXAMPLE 1

Preparation of Hydrazinecarboxylic acid, 4-amino-4-carboxybutyl ester

Step A: 2-(N-t-Butyloxycarbonylamino)-5-(O-chloroformate)-5-hydroxynorvaline, t-butyl ester Dissolve 5-hydroxynorvaline (13.3 g, 0.1 mol) in 1N sodium hydroxide (200 mL, 0.2 mol). Add a solution of $CuSO_4 \cdot 5H_2O$ (12.5 g, 0.05 mol) in water (50 mL). Stir the mixture until solution is complete. Treat with benzyl bromide (17.1 g, 0.1 mol) and stir at room temperature until reaction is complete. Suction filter, wash the residue with 1:3.5 methanol-water and dry at 60° C. to give the copper complex. Suspend the copper complex in water, treat with excess hydrogen sulfide, heat to boiling, then cool to room temperature. Mix with 1N sodium hydroxide and filter. Stir the filtrate with a slight excess of 1N hydrochloric acid and filter. Wash the residue with water and dry to give O-benzyl-5-hydroxynorvaline.

Suspend O-benzyl-5-hydroxynorvaline (67 g, 0.3 mol) in t-butyl acetate (250 mL) and cool to 10° C. Add p-toluenesulfonic acid (57 g, 0.3 mol) and add, by dropwise addition, concentrated sulfuric acid (80 mL). Stir at 10° C. until the reaction is complete, basify to pH 8 by adding a suspension of sodium bicarbonate in water. Extract with ethyl acetate, dry ($MgSO_4$), and evaporate to give O-benzyl-5-hydroxynorvaline, t-butyl ester. Dissolve O-benzyl-5-hydroxynorvaline, t-butyl ester (2.79 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry ($MgSO_4$) and blow to a residue with a stream of nitrogen to give N-t-butyloxycarbonyl-O-benzyl-5-hydroxynorvaline, t-butyl ester.

Mix N-t-butyloxycarbonyl-O-benzyl-5-hydroxynorvaline, t-butyl ester (2.0 g, 5.3 mmol) and 10% palladium/carbon (0.5 g) in 95% ethanol (40 mL). Hydrogenate at room temperature at atmospheric pressure. Filter and evaporate the filtrate in vacuo to give N-t-butyloxy-5-hydroxynorvaline, t-butyl ester.

Dissolve N-t-butyloxy-5-hydroxynorvaline, t-butyl ester (2.89 g, 10 mmol) in methylene dichloride (50 mL), place under a nitrogen atmosphere and cool to 0° C. Add phosgene (1.0 g, 10 mmol) and allow to stir at room temperature for 2 hours to give the crude title compound.

Step B: N-t-Butyl-5-(hydazinoamide)-5-hydroxynorvaline, t-butyl ester

Add hydrazine (0.5 g, 15 mmol) to 2-(N-t-butyloxycarbonyl-amino)-5-(O-chloroformate)-5-hydroxynorvaline, t-butyl ester(3.51 g, 10 mmol) and stir at room temperature for 8 hours. Pour the reaction mixture into water and separate the organic phase. Extract the aqueous phase with ethyl acetate (2×), wash the combined organic phases with saturated sodium chloride and dry ($MgSO_4$). Evaporate the solvent in vacuo and purify by silica gel chromatography to give the title compound.

Step C: Hydrazinecarboxylic acid, 4-amino-4-carboxybutyl ester

Mix N-t-butyl-5-hydazinoamide)-5-hydroxynorvaline, t-butyl ester (3.47 g, 10 mmol) and 1N hydrochloric acid (50 mL) and stir under a nitrogen atmosphere at room temperature for 4 hours. Pour the reaction mixture into ethyl ether and separate the aqeous phase. Wash the aqueous phase with ethyl ether (2×), the neutralize with 5N sodium hydroxide. Evaporate the water in vacuo then purify by ion-exchange chromatography to give the title compound.

EXAMPLE 2

Preparation of 6-[[(Cyclopropylamino)carbonyl]oxy]-norleucine

Step A: 2-(N-t-Butyloxycarbonylamino)-6-(O-chloroformate)-6-hydroxynorleucine, t-butyl ester Dissolve 6-hydroxynorleucine (14.7 g, 0.1 mol) in 1N sodium hydroxide (200 mL, 0.2 mol). Add a solution of $CuSO_4 \cdot 5H_2O$ (12.5 g, 0.05 mol) in water (50 mL). Stir the mixture until solution is complete. Treat with benzyl bromide (17.1 g, 0.1 mol) and stir at room temperature until reaction is complete. Suction filter, wash the residue with 1:3.5 methanol-water and dry at 60° C. to give the copper complex. Suspend the copper complex in water, treat with excess hydrogen sulfide, heat to boiling, then cool to room temperature. Mix with 1N sodium hydroxide and filter. Stir the filtrate with a slight excess of 1N hydrochloric acid and filter. Wash the residue with water and dry to give O-benzyl-6-hydroxynorleucine.

Suspend O-benzyl-6-hydroxynorleucine (71.2 g, 0.3 mol) in t-butyl acetate (250 mL) and cool to 10° C. Add p-toluenesulfonic acid (57 g, 0.3 mol) and add, by dropwise addition, concentrated sulfuric acid (80 mL). Stir at 10° C. until the reaction is complete, basify to pH 8 by adding a suspension of sodium bicarbonate in water. Extract with ethyl acetate, dry (MgSO$_4$), and evaporate to give O-benzyl-6-hydroxynorleucine, t-butyl ester.

Dissolve O-benzyl-6-hydroxynorleucine, t-butyl ester (2.93 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO$_4$) and blow to a residue with a stream of nitrogen to give N-t-butyloxycarbonyl-O-benzyl-6-hydroxynorleucine, t-butyl ester.

Mix N-t-butyloxycarbonyl-O-benzyl-6-hydroxynorleucine, t-butyl ester (2.0 g, 5.1 mmol) and 10% palladium/carbon (0.5 g) in 95% ethanol (40 mL). Hydrogenate at room temperature at atmospheric pressure. Filter and evaporate the filtrate in vacuo to give N-t-butyloxy-6-hydroxynorleucine, t-butyl ester.

Dissolve N-t-butyloxy-6-hydroxynorleucine, t-butyl ester (3.03 g, 10 mmol) in methylene dichloride (50 mL), place under a nitrogen atmosphere and cool to 0° C. Add phosgene (1.0 g, 10 mmol) and allow to stir at room temperature for 2 hours to give the crude title compound.

Step B: N-t-Butyl-6-(cyclopropylamide)-6-hydroxynorleucine, t-butyl ester

Add cyclopropylamine (0.86 g, 15 mmol) to 2-(N-t-butyloxycarbonylamino)-6-(O-chloroformate)-6-hydroxynorleucine, t-butyl ester (3.65 g, 10 mmol) and stir at room temperature for 8 hours. Pour the reaction mixture into water and separate the organic phase. Extract the aqueous phase with ethyl acetate (2×), wash the combined organic phases with saturated sodium chloride and dry (MgSO$_4$). Evaporate the solvent in vacuo and purify the by silica gel chromatography to give the title compound.

Step C: 6[[(Cyclopropylamino)carbonyl]oxy]-norleucine

Mix N-t-butyl-6-(cyclopropylamide)-6-hydroxynorleucine, t-butyl ester (3.86 g, 10 mmol) and 1N hydrochloric acid (50 mL) and stir under a nitrogen atmosphere at room temperature for 4 hours. Pour the reaction mixture into ethyl ether and separate the aqeous phase. Wash the aqueous phase with ethyl ether (2×), the neutralize with 5N sodium hydroxide. Evaporate the water in vacuo then purify by ion-exchange chromatography to give the title compound.

EXAMPLE 3

Preparation of Hydrazinecarboxylic acid, 4-amino-4-carboxy-2-butenyl ester

Step A: 2-(N-t-Butyloxycarbonylamino)-5-(O-chloroformate)-3-pentenoic acid, t-butyl ester Dissolve dimethyl 2-acetimido-2-(3-hydroxy-1-propene) malonate (*Tetrahedron. Lett.*, 29(47), 6183–4 (1988) (2.45 g, 10 mmol) in tetrahydrofuran (30 mL). Treat with 1N sodium hydroxide and stir at room temperature until hydrolysis of the esters is complete. Acidify with 5N hydrochloric acid and stir at 50° C. until decarboxylation is complete. Cool to room temperature pour into methylene chloride and separate the organic phase. Extract the aqueous phase with methylene chloride (2×), dry (MgSO$_4$) and evaporate the solvent in vacuo to give 5-hydroxy-2-(acetamido)-3-pentenoic acid.

Mix 5-hydroxy-2-(acetamido)-3-pentenoic acid (1.73 g, 10 mmol) and acylase (I) (Merck) in pH 7.2 buffer and stir at 37° C. until hydrolysis is complete. Purify by ion exchange chromatography to give 5-hydroxy-2-amino-3-pentenoic acid.

Dissolve 5-hydroxy-2-amino-3-pentenoic acid (13.1 g, 0.1 mol) in 1N sodium hydroxide (200 mL, 0.2 mol). Add a solution of CuSO$_4$.5H$_2$O (12.5 g, 0.05 mol) in water (50 mL). Stir the mixture until solution is complete. Treat with benzyl bromide (17.1 g, 0.1 mol) and stir at room temperature until reaction is complete. Suction filter, wash the residue with 1:3.5 methanol-water and dry at 60° C. to give the copper complex. Suspend the copper complex in water, treat with excess hydrogen sulfide, heat to boiling, then cool to room temperature. Mix with 1N sodium hydroxide and filter. Stir the filtrate with a slight excess of 1N hydrochloric acid and filter. Wash the residue with water and dry to give O-benzyl-5-hydroxy-2-amino-3-pentenoic acid.

Suspend O-benzyl-5-hydroxy-2-amino-3-pentenoic acid (66.4 g, 0.3 mol) in t-butyl acetate (250 mL) and cool to 10° C. Add p-toluenesulfonic acid (57 g, 0.3 mol) and add, by dropwise addition, concentrated sulfuric acid (80 mL). Stir at 10° C. until the reaction is complete, basify to pH 8 by adding a suspension of sodium bicarbonate in water. Extract with ethyl acetate, dry (MgSO$_4$), and evaporate to give O-benzyl-5-hydroxy-2-amino-3-pentenoic acid, t-butyl ester.

Dissolve O-benzyl-5-hydroxy-2-amino-3-pentenoic acid, t-butyl ester (2.77 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO$_4$) and blow to a residue with a stream of nitrogen to give 2-(N-t-butyloxycarbonylamino)-5-(O-benzyloxy)-3-pentenoic acid, t-butyl ester.

Mix 2-(N-t-butyloxycarbonylamino)-5-(O-benzyloxy)-3-pentenoic acid, t-butyl ester (2.0 g, 5.3 mmol) and 10% palladium/carbon (0.5 g) in 95% ethanol (40 mL). Hydrogenate at room temperature at atmospheric pressure. Filter and evaporate the filtrate in vacuo to give 2-(N-t-butyloxycarbonylamino)-5-hydroxy-3-pentenoic acid, t-butyl ester.

Dissolve 2-(N-t-butyloxycarbonylamino)-5-hydroxy-3-pentenoic acid, t-butyl ester (2.87 g, 10 mmol) in methylene dichloride (50 mL), place under a nitrogen atmosphere and cool to 0° C. Add phosgene (1.0 g, 10 mmol) and allow to stir at room temperature for 2 hours to give the title compound.

Step B: 5-(O-Hydrazinoamide)-2-(N-t-butyloxyamino)-5-hydroxy-3-pentenoic acid, t-butyl ester Add hydrazine (0.5 g, 15 mmol) to 2-(N-tert-butyloxycarbonylamino)-5-(O-chloroformate)-3-pentenoic acid, t-butyl ester (3.5 g, 10 mmol) and stir at room temperature for 8 hours. Pour the reaction mixture into water and separate the organic phase. Extract the aqueous phase with ethyl acetate (2×), wash the combined organic phases with saturated sodium chloride and dry (MgSO$_4$). Evaporate the solvent in vacuo and purify the by silica gel chromatography to give the title compound.

Step C: Hydrazinecarboxylic acid, 4-amino-4-carboxy-2-butenyl ester

Mix 5-(O-hydrazinoamide)-2-(N-t-butyloxyamino)-5-hydroxy-3-pentenoic acid, t-butyl ester (3.45 g, 10 mmol) and 1N hydrochloric acid (50 mL) and stir under a nitrogen atmosphere at room temperature for 4 hours. Pour the reaction mixture into ethyl ether and separate the aqeous phase. Wash the aqueous phase with ethyl ether (2×), the neutralize with 5N sodium hydroxide. Evaporate the water in vacuo then purify by ion-exchange chromatography to give the title compound.

Those compounds of Formula Ib in which Z is represented by $NR_1$ can also be made using techniques known in the art. Reaction Scheme II shows one method by which these compounds can be produced.

be optionally purified by flash chromatography. In Step B these protecting groups are removed by an acidic hydrolysis. This hydrolysis can be carried out in the same manner as the deprotection reaction of Reaction Scheme I. The deprotected compound of Formula Ib can be purified by either ion exchange chromatography or by preparative $C_{18}$ reverse phase chromatography. Likewise, the appropriate R substituent may be placed on the compound of Formula Ib utilizing the same methods as taught in Reaciton Scheme I.

If Pr and Pr' are represented by either hydrogen atoms or by a copper complexm, then the displacement reaction is

REACTION SCHEME II

STEP A

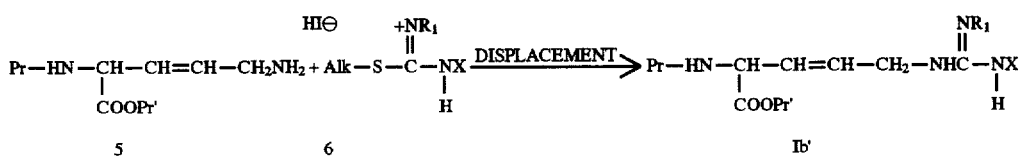

STEP B

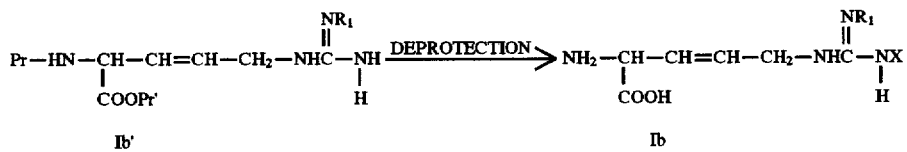

STEP C

In Step A, a displacement reaction is carried out between a functionalized amino acid as described by structure (5) and an amidino derivative as described by structure (6). In the amidine structure (6), Alk is represented by a $C_{1-4}$ alkyl, and $R_1$ and X are as defined in Formula Ia. This displacement reacation produces the optionally protected compound which has been depicted as Ib'. In step B, the protecting groups, if present, are removed via an acidic hydrolysis and in Step C the appropriate R substituent may be placed on the molecule as is depicted.

The displacement reaction of Step A can be carried out using techniques well known in the art. The meanings for Pr and Pr' should be complementary (i.e. both should be hydrogen, organic residues or copper). The appropriate amidine (6) is one in which X is represented by the substituent which is desired in the final product. The linear $C_{1-4}$ alkyl represented by Alk is not retained in the final product, and thus its identity is immaterial.

The particular manner in which the displacement reaction is carried out depends upon the particular substituent which is present at the Pr and Pr' position. If Pr and Pr' are represented by organic protecting groups, then the reaction is carried out be contacting approximately equivalent amounts of the functionalized amino acid and the amindino- derivative in an aprotic solvent such as dimethylformamide at a temperature range of from room temperature to about 80° C. The reaction is typically allowed to proceed for a period of time ranging from about 8 hours to about 120 hours. Upon completion of the reaction, the functionalized amino acid of Formula Ib' can be recovered by either concentration or extraction as is known in the art. It can then carried out in the following manner. Approximately equivalent amounts of the functionalized amino acid of structure (5) and the amidino derivative of structure (6) are contacted in a dilute solution of an inorganic base such as sodium hydroxide. The displacment reaction is carried out at about 40° C. for a period of time ranging from about 8 to 120 hours. The desired product of Formula Ib can then be recovered from the reaction by either extraction or concentration as is known in the art. This crude product can then be purrified by ion exchange chromatography or by preparative $C_{18}$ reverse phase chromatography.

Methods for preparing the functionalized amino acids of structure (5) are well known in the art. For example, 5-amino-2-(N-acetylamino)-3-pentenoic acid is described in Tetrahedron Letters, 29(47), 6183–4 (1988). Methods for preparing the amidino derivatives of structure (6) are also well known in the art. For examples, see G. V. Nair, Ind. J. Chem., 4, 516 (1966).

The following example presents a typical synthesis as described above in Scheme II. This example is understood to be illustrative only and is not intended to limit the scope of the present invention in any way.

EXAMPLE 4

Preparation of 2-Amino-5-[(hydrazinoiminomethyl) amino-3-pentenoic acid

Step A: $N^5$-[Hydrazino-iminomethyl]-2-(acetylamino)-5-amino-3-pentenoic acid

Mix 5-amino-2-(N-acetylamino)-3-pentenoic acid HCl (4.16 g, 20 mmol) and S-methylisothiosemicarbazide (2.11 g, 20 mmol) in 1N NaOH (40 mL) and stir under a blanket of $N_2$ at 40° C. for 48 hours. Cool the reaction to room temperature, neutralize with 1N HCl and blow to a residue with a stream of $N_2$ to give the title compound.

Step B: 2-Amino-5-[(hydrazinoiminomethyl)amino]-3-pentenoic acid

Mix $N^5$-[hydrazino-iminomethyl]-2-(acetylamino)-5-amino-3-pentenoic acid (4.6 g, 20 mmol) and acylase (I) (Merck) in pH 7.2 buffer and stir at 37° C. until hydrolysis is complete. Purify by ion exchange chromatography to give the title compound.

Alternatively, those compounds of Formula Ib in which Z is represented by O can be made utilizing the methods disclosed in Reaction Scheme IV. The only modification is that the functionalized amino acid that is utilized as one of the starting materials should have a double bond connecting the α and β carbon atoms. This starting material may be represented by the following formula:

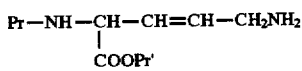

in which Pr and Pr' are as above.

Those compounds of Formula Ic in which Z is represented by NR1 can also be made using techniques known in the art. Reaction Scheme III shows one method by which these compounds can be produced.

removed via an acidic hydrolysis and in Step C the appropriate R substituent may be placed on the molecule as is depicted.

The displacement reaction of Step A can be carried out using techniques well known in the art. The appropriate functionalized amino acid of structure (7) is one in which W' corresponds to the substituent which is desired at this position in the final product (i.e. if W is to be represented by —$CH_2$—NH—, then W' should be represented by —$CH_2$—$NH_2$). The meanings for Pr and Pr' should be complementary (i.e. both should be hydrogen, organic residues or copper). The appropriate amidine is one in which X is represented by the substituent which is desired in the final product. The linear $C_{1-4}$ alkyl represented by Alk is not retained in the final product, and thus its identity is immaterial.

The particular manner in which the displacement reaction is carried out depends upon the particular substituent which is present at the Pr and Pr' position. If Pr and Pr' are represented by organic protecting groups, then the reaction is carried out by contacting approximately equivalent amounts of the functionalized amino acid and the amidino-derivative in an aprotic solvent such as dimethylformamide at a temperature range of from room temperature to about 80° C. The reaction is typically allowed to proceed for a period of time ranging from about 8 hours to about 120 hours. Upon completion of the reaction, the functionalized amino acid of formula Ic' can be recovered by either

REACTION SCHEME III

STEP A

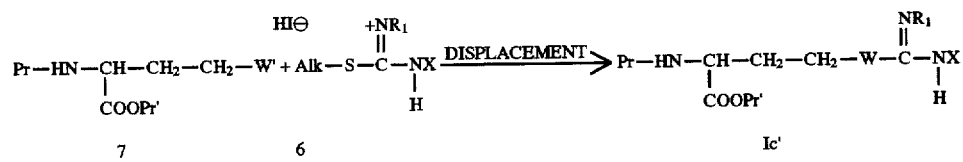

STEP B

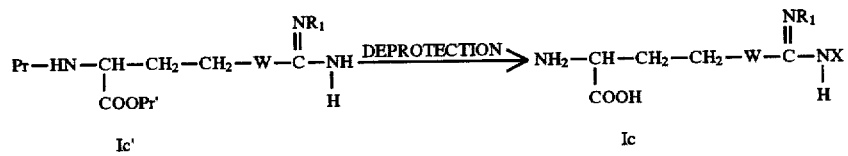

STEP C

In Step A, a displacement reaction is carried out between a functionalized amino acid as described by structure (7) and an amidino derivative as described by structure (6). In structure (7), W' is represented by —$CH_2$—$NH_2$, —NH—$NH_2$, —$CH_2$—O—$NH_2$, —$CH_2$—NH—$NH_2$, —$(CH_2)_2$—$NH_2$ or —O—$NH_2$. If W' is represented by —$CH_2$—NH then Pr and Pr may both be hydrogen or copper. Alternatively Pr' is t-butyl while Pr is t-butyloxycarbonyl. If W' is either $NH_2$—$NH_2$—, —$CH_2$—O—$NH_2$, —$CH_2$—NH—$NH_2$, or O—$NH_2$—, then Pr and Pr' may both be copper, or Pr' is ethyl while Pr is a benzyloxycarbonyl. In structure (6), Alk is represented by a $C_{1-4}$ alkyl, and $R_1$ and X are as defined in Formula Ic. This displacement reaction produces the optionally protected compound which has been depicted as Ic'. In step B, the protecting groups, if present, are concentration or extraction as is known in the art. It can then be optionally be purified by flash chromatography. In Step B these protecting groups are removed by an acidic hydrolysis. This hydrolysis can be carried out in the same manner as the deprotection reaction of Reaction Scheme I. The deprotected compound of Formula Ic can be purified by either ion exchange chromatography or by preparative $C_{18}$ reverse chromatography. Likewise, the appropriate R substituent may be placed on the compound of Formula Ic utilizing the same methods as taught in Reaction Scheme I.

If Pr and Pr' are represented by either hydrogen atoms or by a copper complex then the displacement reaction is carried out in the following manner. Approximately equivalents amounts of the functionalized amino acid of structure (7) and the amidino derivative of structure (6) are contacted in a dilute solution of an inorganic base such as sodium hydroxide. The displacement reaction is carried out at about 40° C. for a period of time ranging from about 8 to 120 hours. The desired product of Formula Ic can then be recovered from the reaction by either extraction or concentration as is known in the art. This crude product can then be purified by ion exchange chromatography or by preparative $C_{18}$ reverse chromatography.

Methods for producing the functionalized amino acids of structure (7) are known in the art. For example, the preparation of canaline is described in *J. Am. Chem. Soc.*, 79, 1222 (1957).

The following examples represent typical syntheses as described above in Scheme III. These examples are intended to be illustrative only and are not intended to limit the scope of the present invention in any way.

EXAMPLE 5

Preparation of $N^5$-[Imino(2-methyl-hydrazino) methyl]-L-ornithine, flavinate

This example demonstrates the preparation of a compound according to formula Ic in which Z is N, utilizing the methodology of Reaction Scheme III.

L-Ornithine HCl (3.36 g, 20 mmol) and S-methyl-4-methylisothiosemicarbazide hydroiodide (5.00 g, 20 mmol) in 1M NaOH (40 ml) were mixed and stirred under a blanket $N_2$ at 40° C. (for 48 hours. The reaction was then neutralized with 1M HCl and blown to a residue with a stream of $N_2$. The residue was applied to a Dowex AG50-X8 column and eluted with 0.2M $NH_4OH$. The fractions containing the desired product were lyophilized and the resulting solid taken up in water (20 ml). Flavianic acid (3.2 g) in water (20 ml) was added and the solution cooled to 4° C. for 16 hours. The resulting solid was filtered and crystallized from water to yield 1.3 g of the title compound as a yellow solid. $^1$HNMR (300 $MH_2$, $\delta_6$ DMSO) 1.45 (2,m) 1.78 (2,m) 2.85 (3,s) 3.15 (2m) 3.85 (1,t) 7.8 (1,m) 8.6–8.8 (2,m) 9.2 (1,s). Anal. Cald. for $C_{17}H_{23}N_7O_{10}S$: C, 39.46; H, 4.48; N, 18.95. Found C, 38.56; H, 4.48; N, 18.95.

EXAMPLE 6

Preparation of $N^5$-[(Cyclopropylamino)-iminomethyl]-L-ornithine, flavinate

This example also demonstrates the methodology of Reaction Scheme III.

t-Butyl isothiocyanate (11.6 ml, 0.1 mol) and cyclopropylamine (6.9 ml, 0.1 mol) were mixed in toluene (200 ml) and stirred at room temperature overnight. The resulting mixture was evaporated to a residue and crystallized from cyclohexane to yield N-cyclopropyl-N-butyl thiourea. N-cyclopropyl-N-t-butyl thiourea (5 g) was suspended in 5M HCl (50 ml) and heated to 80° C. for 10 minutes. The resulting solution was cooled, poured into a saturated sodium bicarbonate (250 ml), and extracted with ethyl acetate (2×125 ml). The solution was dried ($MgSO_4$), evaporated to a residue and crystallized from ethyl acetate to yield a white solid, cyclopropyl thiourea, 110 mg.

Cyclopropyl thiourea (0.65 g, 0.0056 mol) and iodomethane (1.2 g, 0.0085 mol) were mixed in acetone, heated to boiling and refluxed for 15 minutes. The reaction was cooled and blown to an oil. Ethyl acetate (10 ml) was added, and the resulting mixture was blown to a white solid. L-Ornithine.HCl (0.94 g, 0.0056 mol) and 1M NaOH (15 ml) were added and the resulting reaction warmed to 40° C. and stirred under a blanket of $N_2$ for 16 hours. The reaction mixture was cooled to room temperature, acidified with acetic acid and blown with a stream of $N_2$ to ½ volume. Flavianic acid (1 g) in water (10 ml) was added and the resulting solid filtered, dried and recrystallized from boiling water to yield 1.4 g of the title compound which appeared as a yellow solid. $^1$HNMR ($d_6$DMSO) 0.52 (2,m) 0.82 (2,m) 1.45 (2m) 1.78 (2,m) 2.5 (1,m) 3.15 (2,m) 3.85 (1,m) 7.8 (1,m) 8.1–8.8 (2,m) 9.2 (1,s). Anal Calcd. for $C_9H_{18}N_4O_2 \cdot C_{10}H_6N_2O_8S \cdot 1/2H_2O$: C, 41.97; H, 4.64; N, 15.76. Found C, 42.67; H, 4.56; N, 15.76.

EXAMPLE 7

Preparation of 2-Amino-4-[2-(hydrazinoiminomethyl)hydrazino]-butanoic acid, flavinate Mix canaline (2.65 g, 20 mmol) and S-methylisothiosemicarbazide hydroiodide (4.66 g, 20 mmol) in 1M NaOH (40 ml) and stir under a blanket $N_2$ at 40° C. for 48 hours. Neutralize the reaction with 1M HCl and blow to a residue with a stream of $N_2$. Apply the residue to a Dowex AG50-X8 column and elute with 0.2M $NH_4OH$. Lyophilize the fractions containing the desired product and take up the resulting solid in water (20 ml). Add flavianic acid (3.2 g) in water (20 ml) and cool the solution to 4° C. for 16 hours. Filter the resulting solid and crystallize to yield the title compound.

EXAMPLE 8

Preparation of $N^5$-(Hydrazino-iminomethyl)-L-ornithine, flavinate

Mix lysine HCl (3.65 g, 20 mmol) and S-methyl-isothiosemicarbazide hydroiodide (4.66 g, 20 mmol)and adjust to pH 10 with 1M NaOH. Stir under a blanket $N_2$ at 40° C. (for 48 hours. Neutralize the reaction with 1M HCl and blow to a residue with a stream of $N_2$. Apply the residue to a Dowex AG50-X8 column and elute with 0.2M $NH_4OH$. Lyophilize the fractions containing the desired product and dissolve the resulting solid in water (20 ml). Add a solution of flavianic acid (3.2 g) in water (20 ml) and cool to 4° C. for 16 hours. Filter the resulting solid and crystallize from water to yield 1.2 g of the title compound. $^1$HNMR ($d_6$DMSO) 1.3–1.6 (4,m), 1.85 (2,m), 3.15 (2,m), 3.95 (1,t), 8.05 (2,m), 8.8 (3,m), 9.2 (1,m); $^{13}$CNMR ($d_6$DMSO) 22.3, 28.7, 30.2, 41.04, 52.0, 57.4, 124.7, 125.2, 129.1, 129.6, 130.3, 130.7, 132.0, 144.5, 158.8, 168, 172.1, 174.1.

EXAMPLE 9

Preparation of O-[(Hydrazinoimino-methyl)amino]-L-homoserine

Dissolve 5-hydroxynorvaline (20 g, 0.15 mol) in water (90 mL) and add anhydrous potassium carbonate (10.4 g, 0.075 mol) with stirring. Heat the slightly alkaline solution on a steam-bath for a few minutes, then add a solution of potassium cyanate (13.0 g, 0.16 mol) in water (50 mL). Heat the final solution on a steam-bath for 2 hours. Treat the solution with 48% hydrobromic acid (100 mL) and heat for an additional 2 hours on the steam-bath. Evaporate the solvent in vacuo and digest the residue with hot acetone (150 mL) and filter. Wash the potassium bromide residue with hot acetone until white. Evaporate the acetone filtrate and heat the residue with additional 48% hydrobromic acid for 2 hours on the steam-bath. Evaporate the solvent in vacuo, dissolve the residue in hot water (75 mL), bring to pH 5–6 with concentrated ammonia, filter, cool and collect 5-(3-bromopropyl)-hydantoin.

Dissolve 85% potassium hydroxide (3.96 g, 60 mmol) in absolute ethanol (60 mL). Add 5-(3-bromopropyl)hydantoin (6.63 g, 30 mmol) and a solution of hydroxyurethane (6.30 g, 60 mmol) in absolute ethanol (40 mL). Reflux for 3 hours, cool and filter to remove potassium bromide. Evaporate the solvent in vacuo, dissolve the residue in water (30 mL), neutralize with dilute hydrochloric acid, cool and collect 5-[3-(carbethoxyaminooxy)-propyl]-hydantoin.

Mix 5-[3-(carbethoxyaminooxy)-propyl]-hydantoin (2.45 g, 10 mmol), barium hydroxide octahydrate (18.15 g, 10 mmol) and water (55 mL). Reflux for 12 hours, remove the white solid by filtration, extract the filter cake with boiling water (25 ml) and finally wash with hot water (25 mL). Combine the filtrate and washings, treat with ammonium carbonate (5.7 g) and heat with stirring. Filter off the barium carbonate, wash the filter cake with hot water and evaporate the filtrate and washings in vacuo to give 2-amino-5-aminooxy-pentanoic acid.

Mix 2-amino-5-aminooxy-pentanoic acid (2.97 g, 20 mmol) and S-methyl-isothiosemicarbazide hydroiodide (4.66 g, 20 mmol) in 1M NaOH (40 ml) and stir under a blanket $N_2$ at 40° C. (for 48 hours). Neutralize the reaction with 1M HCl and blow to a residue with a stream of $N_2$. Apply the residue to a Dowex AG50-X8 column and elute with 0.2M $NH_4OH$. Lyophilize the fractions containing the desired product and take up the resulting solid in water (20 ml). Add flavianic acid (3.2 g) in water (20 ml) and cool the solution to 4° C. for 16 hours. Filter the resulting solid and crystallize to yield the title compound.

An alternative method for producing the compounds of Formula Ic in which Z is represented by $NR_1$ and $R_1$ is hydrogen, is to carry out a displacement reaction between a functionalized amino acid as described by structure (7) in which Pr and Pr' are represented by protecting groups and an amino nitrile of the Formula, X—NH—CN, in which X is as defined in Formula Ic. This displacement reaction produces the protected compound of Formula Ic' disclosed above in Reaction Scheme III. This displacement can be carried out by contacting equivalent amounts of the reactants in an aprotic solvent such as toluene or benzene at a temperature of about −5° C. to reflux for a period of time ranging from about 1 hour to 16 hours. The compound of Formula Ic' can be recovered by either extraction or concentration. It can then be purified by ion exchange chromatography or preparation $C_{18}$ reverse phase chromatography. The desired compounds of Formula Ic can then be produced via the deprotection reaction and optional functionalization reactions taught in steps B and C of Reaction Scheme II. Those compounds of Formula Ic in which Z is represented by O can also be produced by methods known in the art. One such method is disclosed below in Reaction Scheme IV:

REACTION SCHEME IV

STEP A

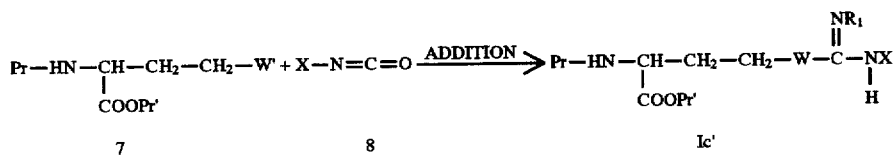

STEP B

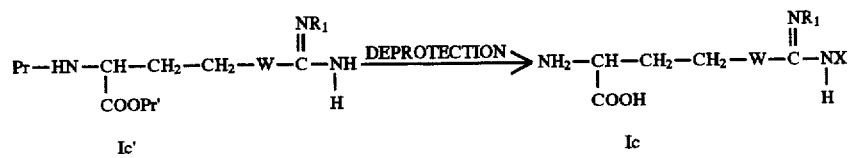

STEP C

In Step A an addition reaction is carried out between a functionalized amino acid as described by structure (7) in which Pr, Pr' and W' are as defined in Reaction Scheme III, and an isocyanate derivative as described by structure (8) in which X is as defined in Formula Ic and Z is O as is depicted. This addition reaction produces the protected compound of Formula Ic'. The deprotection reaction of Step B produces the desired compound of Formula Ic. If desired this compound can be subjected to the optional functionalization reaction of Step C.

The appropriate isocyanate derivative is one in which X is represented by the same substituent as is desired in the final product of Formula Ic. The addition reaction of Step A can be carried out using techniques well known in the art. Typically approximately equivalent amounts of the reactants are contacted in an organic solvent such as toluene, benzene, or methylene dichloride at a temperature range of from −10° C. to about 80° C. for a period of time ranging from about 1 to 16 hours. The protected compound of Formula Ic' can then be recovered from the reaction by either concentration or extraction as is known. It can then be purified by flash chromatography. The deprotection reaction of Step B and the optional functionalization reaction of Step C can be carried out using the methods taught in the previous Reaction Schemes.

Those compounds of Formula Ic in which Z is represented by O and W is represented by either —$CH_2$—NH— or

19

—(CH$_2$)$_2$—NH— can also be made by the following alternative method. A displacement reaction is carried out between phosgene (previous structure 2 of Reaction Scheme I, Y=Cl) or triphosgene (previous structure 2 of Reaction Scheme I, Y=OCCl$_3$) and a functionalized amino acid of the formula: in which W' is represented by either —CH$_2$—NH$_2$ or —(CH$_2$)$_2$—NH$_2$ and in which Pr and Pr' are as defined above Reaction Scheme

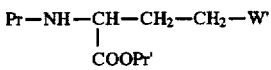

I. This displacement reaction can be carried out using techniques known in the art. Typically approximately equivalent amounts of the reactants are contacted in an organic solvent solvent such as toluene, benzene or methylene dichloride at a temperature range of from −10° C. to 60° C. The reaction is usually allowed to proceed for a period of time ranging from about 1 to 16 hours At this point, a molar excess of an amine of the formula, NH$_2$X, in which X is as defined in Formula Ic, is added to the reaction. The reactants are heated to a temperature range of −10° C. to 60° C. for a period of time ranging from 1 to 16 hours. This reaction produces a product which can be described by Formula Ic' in Reaction Scheme III in which W is represented by CH$_2$—NH, and X, Pr and Pr' are as above, and Z is represented by O as is depicted. These compounds can then be subjected to a deprotection reaction and an optional functionalization reaction in the same manner as disclosed in Reaction Scheme III.

The following examples represent typical syntheses as described above for compounds of formula Ic, wherein Z is O, W is —(CH$_2$)$_2$NH—, and X is NH$_2$. These examples are intended to be illustrative only and are not intended to limit the scope of the present invention in any way.

EXAMPLE 10

Preparation of N$^5$-(Hydrazinocarbonyl)-L-ornithine

Step A: N-t-Butyloxycarbonyl-N$^5$-(trichlormethylcarbonate)-ornithine, t-butyl ester Dissolve ornithine (13.3 g, 0.1 mol) in 1N sodium hydroxide (200 mL, 0.2 mol). Add a solution of CuSO$_4$.5H$_2$O (12.5 g, 0.05 mol) in water (50 mL). Stir the mixture until solution is complete. Treat with benzyl chloroformate (17.1 g, 0.1 mol) and stir at room temperature until reaction is complete. Suction filter, wash the residue with 1:3.5 methanol-water and dry at 60° C. to give the copper complex. Suspend the copper complex in water, treat with excess hydrogen sulfide, heat to boiling, then cool to room temperature. Mix with 1N sodium hydroxide and filter. Stir the filtrate with a slight excess of 1N hydrochloric acid and filter. Wash the residue with water and dry to give N$^5$-benzyloxycarbonyl-ornithine.

Suspend N$^5$-benzyloxycarbonyl-ornithine (80 g, 0.3 mol) in t-butyl acetate (250 mL) and cool to 10° C. Add p-toluenesulfonic acid (57 g, 0.3 mol) and add, by dropwise addition, concentrated sulfuric acid (80 mL). Stir at 10° C. until the reaction is complete, basify to pH 8 by adding a suspension of sodium bicarbonate in water. Extract with ethyl acetate, dry (MgSO$_4$), and evaporate to give N$^5$-benzyloxycarbonyl-ornithine, t-butyl ester.

Dissolve N$^5$-benzyloxycarbonyl-ornithine, t-butyl ester (3.22 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO$_4$) and blow to a residue with a stream of nitrogen to give N-t-butyloxycarbonyl-N$^5$-benzyloxycarbonyl-ornithine, t-butyl ester.

Mix N-t-butyloxycarbonyl-N$^5$-benzyloxycarbonyl-ornithine, t-butyl ester (2.0 g, 5.0 mmol) and 10% palladium/carbon (0.5 g) in 95% ethanol (40 mL). Hydrogenate at room temperature at atmospheric pressure. Filter and evaporate the filtrate in vacuo to give N-t-butyloxycarbonyl-ornithine, t-butyl ester.

Dissolve N-t-butyloxycarbonyl-ornithine, t-butyl ester (2.88 g, 10 mmol) in methylene dichloride (30 mL), place under a nitrogen atmosphere and cool to 0° C. Add triphosgene (2.81 g, 10 mmol) and allow to stir at room temperature for 2 hours to give the crude title compound.

Step B: N$^2$-t-Butyl-N$^5$-hydrazinoamide-ornithine, t-butyl ester

Add hydrazine (0.5 g, 15 mmol) to N-t-butyloxycarbonyl-N$^5$-(trichlormethylcarbonate)-ornithine, t-butyl ester (4.5 g, 10 mmol) and stir at room temperature for 8 hours. Pour the reaction mixture into water and separate the organic phase. Extract the aqueous phase with ethyl acetate (2×), wash the combined organic phases with saturated sodium chloride and dry (MgSO$_4$). Evaporate the solvent in vacuo and purify by silica gel chromatography to give title compound.

Step C: N$^5$-(Hydrazinocarbonyl)-L-ornithine

Mix N$^2$-t-butyl-N$^5$-hydrazinoamide-ornithine, t-butyl ester (3.46 g, 10 mmol) and 1N hydrochloric acid (30 mL) and stir under a nitrogen atmosphere at room temperature for 4 hours. Pour the reaction mixture into ethyl ether and separate the aqueous phase. Wash the aqueous phase with ethyl ether (2×), the neutralize with 5N sodium hydroxide. Evaporate the water in vacuo then purify by ion-exchange chromatography to give the title compound.

EXAMPLE 11

Preparation of N$^6$-(Hydrazinocarbonyl)-L-lysine

Step A: N-t-Butyloxycarbonyl-N$^6$-(trichloromethylcarbonate)-lysine, t-butyl ester Dissolve lysine (14.6 g, 0.1 mol) in 1N sodium hydroxide (200 mL, 0.2 mol). Add a solution of CuSO$_4$.5H2O (12.5 g, 0.05 mol) in water (50 mL). Stir the mixture until solution is complete. Treat with benzyl chloroformate (17.1 g, 0.1 mol) and stir at room temperature until reaction is complete. Suction filter, wash the residue with 1:3.5 methanol-water and dry at 60° C. to give the copper complex. Suspend the copper complex in water, treat with excess hydrogen sulfide, heat to boiling, then cool to room temperature. Mix with 1N sodium hydroxide and filter. Stir the filtrate with a slight excess of 1N hydrochloric acid and filter. Wash the residue with water and dry to give N$^5$-benzyloxycarbonyl-lysine.

Suspend N$^5$-benzyloxycarbonyl-lysine (84.1 g, 0.3 mol) in t-butyl acetate (250 mL) and cool to 10° C. Add p-toluenesulfonic acid (57 g, 0.3 mol) and add, by dropwise addition, concentrated sulfuric acid (80 mL). Stir at 10° C. until the reaction is complete, basify to pH 8 by adding a suspension of sodium bicarbonate in water. Extract with ethyl acetate, dry (MgSO$_4$), and evaporate to give N$^5$-benzyloxycarbonyl-lysine, t-butyl ester.

Dissolve N$^5$-benzyloxycarbonyl-lysine, t-butyl ester (3.36 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO$_4$) and blow to a residue with a stream of nitrogen to give N-t-butyloxycarbonyl-N$^5$-benzyloxycarbonyl-lysine, t-butyl ester.

Mix N-t-butyloxycarbonyl-N$^5$-benzyloxycarbonyl-lysine, t-butyl ester (2.0 g, 4.6 mmol) and 10% palladium/carbon (0.5 g) in 95% ethanol (40 mL). Hydrogenate at room temperature at atmospheric pressure. Filter and evaporate the filtrate in vacuo to give N-t-butyloxycarbonyl-lysine, t-butyl ester.

Dissolve N-t-butyloxycarbonyl-lysine, t-butyl ester (3.02 g, 10 mmol) in methylene dichloride (30 mL), place under a nitrogen atmosphere and cool to 0° C. Add triphosgene (2.81 g, 10 mmol) and allow to stir at room temperature for 2 hours to give the crude title compound.

Step B: N$^2$-t-Butyl-N$^5$-hydrazinoamide-lysine, t-butyl ester

Add hydrazine (0.5 g, 15 mmol) to N-t-butyloxycarbonyl-N$_6$-(trichloromethyl-carbonate)-lysine, t-butyl ester (4.64 g, 10 mmol) and stir at room temperature for 8 hours. Pour the reaction mixture into water and separate the organic phase. Extract the aqueous phase with ethyl acetate (2×), wash the combined organic phases with saturated sodium chloride and dry (MgSO$_4$). Evaporate the solvent in vacuo and purify by silica gel chromatography to give the title compound.

Step C: N$^6$-(Hydrazinocarbonyl)-L-lysine

Mix N$^2$-t-butyl-N$^5$-hydrazinoamide-lysine, t-butyl ester (3.60 g, 10 mmol) and 1N hydrochloric acid (30 mL) and stir under a nitrogen atmosphere at room temperature for 4 hours. Pour the reaction mixture into ethyl ether and separate the aqueous phase. Wash the aqueous phase with ethyl ether (2×), the neutralize with 5N sodium hydroxide. Evaporate the water in vacuo then purify by ion-exchange chromatography to give the title compound.

EXAMPLE 12

Preparation of 2-Amino-4-[2-[(cyclopropylamino) carbonyl]hydrazino]hydrazino-butanoic acid Step A: N-t-Butyloxycarbonyl-2-amino-4-[(trichloromethylcarbonate)hydrazino]-butanoic acid, t-butyl ester Dissolve homoserine (17.9 g, 0.15 mol) in water (90 mL) and add anhydrous potassium carbonate (10.4 g, 0.075 mol) with stirring. Heat the slightly alkaline solution on a steam-bath for a few minutes, then add a solution of potassium cyanate (13.0 g, 0.16 mol) in water (50 mL). Heat the final solution on a steam-bath for 2 hours. Treat the solution with 48% hydrobromic acid (100 mL) and heat for an additional 2 hours on the steam-bath. Evaporate the solvent in vacuo and digest the residue with hot acetone (150 mL) and filter. Wash the potassium bromide residue with hot acetone until white. Evaporate the acetone filtrate and heat the residue with additional 48% hydrobromic acid for 2 hours on the steam-bath. Evaporate the solvent in vacuo, dissolve the residue in hot water (75 mL), bring to pH 5–6 with concentrated ammonia, filter, cool and collect 5-(2-bromoethyl)-hydantoin.

Dissolve 85% potassium hydroxide (3.96 g, 60 mmol) in absolute ethanol (60 mL). Add 5-(2-bromoethyl)hydantoin (6.21 g, 30 mmol) and a solution of ethyl carbazate (6.3 g, 60 mmol) in absolute ethanol (40 mL). Reflux for 3 hours, cool and filter to remove potassium bromide. Evaporate the solvent in vacuo, dissolve the residue in water (30 mL), neutralize with dilute hydrochloric acid, cool and collect 5-(2-(carbethoxyhydrazino)-ethyl)-hydantoin.

Mix 5-[(2-(carbethoxyhydrazino)-ethyl)]-hydantoin (2.3 g, 10 mmol), barium hydroxide octahydrate (18.15 g, 10 mmol) and water (55 mL). Reflux for 12 hours, remove the white solid by filtration, extract the filter cake with boiling water (25 ml) and finally wash with hot water (25 mL). Combine the filtrate and washings, treat with ammonium carbonate (5.7 g) and heat with stirring. Filter off the barium carbonate, wash the filter cake with hot water and evaporate the filtrate and washings in vacuo to give 2-amino-4-hydrazino-butanoic acid.

Dissolve 2-amino-4-hydrazino-butanoic acid (13.3 g, 0.1 mol) in 1N sodium hydroxide (200 mL, 0.2 mol). Add a solution of CuSO$_4$.5H$_2$O (12.5 g, 0.05 mol) in water (50 mL). Stir the mixture until solution is complete. Treat with benzyl chloroformate (17.1 g, 0.1 mol) and stir at room temperature until reaction is complete. Suction filter, wash the residue with 1:3.5 methanol-water and dry at 60° C. to give the copper complex. Suspend the copper complex in water, treat with excess hydrogen sulfide, heat to boiling, then cool to room temperature. Mix with 1N sodium hydroxide and filter. Stir the filtrate with a slight excess of 1N hydrochloric acid and filter. Wash the residue with water and dry to give N$^5$-benzyloxycarbonyl-2-amino-4-hydrazino-butanoic acid.

Suspend N$^5$-benzyloxycarbonyl-2-amino-4-hydrazino-butanoic acid (80.2 g, 0.3 mol) in t-butyl acetate (250 mL) and cool to 10° C. Add p-toluenesulfonic acid (57 g, 0.3 mol) and add, by dropwise addition, concentrated sulfuric acid (80 mL). Stir at 10° C. until the reaction is complete, basify to pH 8 by adding a suspension of sodium bicarbonate in water. Extract with ethyl acetate, dry (MgSO$_4$), and evaporate to give N$^5$-benzyloxycarbonyl-2-amino-4-hydrazino-butanoic acid, t-butyl ester.

Dissolve N$^5$-benzyloxycarbonyl-2-amino-4-hydrazino-butanoic acid, t-butyl ester (3.23 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO$_4$) and blow to a residue with a stream of nitrogen to give N-tert-butyloxycarbonyl-N$^5$-benzyloxycarbonyl-2-amino-4-hydrazino-butanoic acid, t-butyl ester.

Mix N-t-butyloxycarbonyl-N$^5$-benzyloxycarbonyl-2-amino-4-hydrazino-butanoic acid, t-butyl ester (2.11 g, 5.0 mmol) and 10% palladium/carbon (0.5 g) in 95% ethanol (40 mL). Hydrogenate at room temperature at atmospheric pressure. Filter and evaporate the filtrate in vacuo to give N-t-butyloxycarbonyl-2-amino-4-hydrazino-butanoic acid, t-butyl ester.

Dissolve N-t-butyloxycarbonyl-2-amino-4-hydrazino-butanoic acid, t-butyl ester (2.88 g, 10 mmol) in methylene chloride (30 mL), place under a nitrogen atmosphere and cool to 0° C. Add triphosgene (2.81 g, 10 mmol) and allow to stir at room temperature for 2 hours to give the crude title compound.

Step B: N$^2$-t-Butyloxycarbonyl-N$^6$-(cyclopropylamino-carbonyl)-2-amino-4-hydrazino-butanoic acid, t-butyl ester Add cyclopropylamine (0.86 g, 15 mmol) to N-t-butyloxycarbonyl-2-amino-4-[(trichloromethylcarbonate) hydrazino]-butanoic acid, t-butyl ester (4.5 g, 10 mmol) and stir at room temperature for 8 hours. Pour the reaction mixture into water and separate the organic phase. Extract the aqueous phase with ethyl acetate (2×), wash the combined organic phases with saturated sodium chloride and dry (MgSO$_4$). Evaporate the solvent in vacuo and purify by silica gel chromatography to give the title compound.

Step C: 2-Amino-4-[2-Cyclopropylamino)carbonyl] hydrazino]butanoic acid

Mix N$^2$-t-butyloxycarbonyl-N$^6$-(cyclopropylamino) carbonyl)-2-amino-4-hydrazino-butanoic acid, t-butyl ester (3.72 g, 10 mmol) and 1N hydrochloric acid (30 mL) and stir under a nitrogen atmosphere at room temperature for 4 hours. Pour the reaction mixture into ethyl ether and separate the aqueous phase. Wash the aqueous phase with ethyl ether (2×), the neutralize with 5N sodium hydroxide. Evaporate the water in vacuo then purify by ion-exchange chromatography to give the title compound.

EXAMPLE 13

Preparation of 5-[2-(Cyclopropylamino)carbonyl) hydrazino]-norvaline

Step A: N-t-Butyloxycarbonyl-2-amino-5-[ (trichlormethylcarbonate)hydrazino]-pentanoic acid, t-butyl ester Dissolve 85% potassium hydroxide (3.96 g, 60 mmol) in absolute ethanol (60 mL). Add 5-(3-bromopropyl)hydantoin (see Example 9) (6.63 g, 30 mmol) and a solution of ethyl carbazate (6.3 g, 60 mmol) in absolute ethanol (40 mL). Reflux for 3 hours, cool and filter to remove potassium bromide. Evaporate the solvent in vacuo, dissolve the residue in water (30 mL), neutralize with dilute hydrochloric acid, cool and collect 5-[3-(carbethoxyaminooxy)-propyl]-hydantoin.

Mix 5-[3-(carbethoxyhydrazino)-propyl]-hydantoin (2.44 g, 10 mmol), barium hydroxide octahydrate (18.15 g, 10 mmol) and water (55 mL). Reflux for 12 hours, remove the white solid by filtration and extract the filter cake with boiling water (25 ml) and finally wash with hot water (25 mL). Combine the filtrate and washings, treat with ammonium carbonate (5.7 g) and heat with stirring. Filter off the barium carbonate, wash the filter cake with hot water and evaporate the filtrate and washings in vacuo to give 2-amino-5-hydrazino- pentanoic acid.

Dissolve 2-amino-5-hydrazino-pentanoic acid (14.7 g, 0.1 mol) in 1N sodium hydroxide (200 mL, 0.2 mol). Add a solution of CuSO$_4$.5H$_2$O (12.5 g, 0.05 mol) in water (50 mL). Stir the mixture until solution is complete. Treat with benzyl chloroformate (17.1 g, 0.1 mol) and stir at room temperature until reaction is complete. Suction filter, wash the residue with 1:3.5 methanol-water and dry at 60° C. to give the copper complex. Suspend the copper complex in water, treat with excess hydrogen sulfide, heat to boiling, then cool to room temperature. Mix with 1N sodium hydroxide and filter. Stir the filtrate with a slight excess of 1N hydrochloric acid and filter. Wash the residue with water and dry to give N$^7$-benzyloxycarbonyl-2-amino-5-hydrazino-pentanoic acid.

Suspend N$^7$-benzyloxycarbonyl-2-amino-5-hydrazino-pentanoic acid (84.4 g, 0.3 mol) in t-butyl acetate (250 mL) and cool to 10° C. Add p-toluenesulfonic acid (57 g, 0.3 mol) and add, by dropwise addition, concentrated sulfuric acid (80 mL). Stir at 10° C. until the reaction is complete, basify to pH 8 by adding a suspension of sodium bicarbonate in water. Extract with ethyl acetate, dry (MgSO$_4$), and evaporate to give N$^7$-benzyloxycarbonyl-2-amino-5-hydrazino-pentanoic acid, t-butyl ester.

Dissolve N$^7$-benzyloxycarbonyl-2-amino-5-hydrazino-pentanoic acid, t-butyl ester (3.37 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO$_4$) and blow to a residue with a stream of nitrogen to give N-tert-butyloxycarbonyl-N$^7$-benzyloxycarbonyl-2-amino-5-hydrazino-pentanoic acid, t-butyl ester.

Mix N-tert-butyloxycarbonyl-N$^7$-benzyloxycarbonyl-2-amino-5-hydrazino-pentanoic acid, t-butyl ester (2.18 g, 5.0 mmol) and 10% palladium/carbon (0.5 g) in 95% ethanol (40 mL). Hydrogenate at room temperature at atmospheric pressure. Filter and evaporate the filtrate in vacuo to give N-t-butyloxycarbonyl-2-amino-5-hydrazino-pentanoic acid, t-butyl ester.

Dissolve N-t-butyloxycarbonyl-2-amino-5-hydrazino-pentanoic acid, t-butyl ester (2.91 g, 10 mmol) in methylene dichloride (30 mL), place under a nitrogen atmosphere and cool to 0° C. Add triphosgene (2.81 g, 10 mmol) and allow to stir at room temperature for 2 hours to give the crude title compound.

Step B: N$^2$-t-Butyloxycarbonyl-N$^7$-(cyclopropylamino-carbonyl)-2-amino-5-hydrazino-pentanoic acid, t-butyl ester Add cyclopropylamine (0.86 g, 15 mmol) to N-t-butyloxycarbonyl-2-amino-5-[(trichlormethylcarbonate)-hydrazino]-pentanoic acid, t-butyl ester (4.65 g, 10 mmol) and stir at room temperature for 8 hours. Pour the reaction mixture into water and separate the organic phase. Extract the aqueous phase with ethyl acetate (2×), wash the combined organic phases with saturated sodium chloride and dry (MgSO$_4$). Evaporate the solvent in vacuo and purify by silica gel chromatography to give the title compound.

Step C: 5-[2-(Cyclopropylamino)carbonyl]hydrazino]-norvaline pentanoic acid

Mix N$^2$-t-butyloxycarbonyl-N$^7$-(cyclopropylamino-carbonyl)2-amino-5-hydrazino-pentanoic acid, t-butyl ester (3.86 g, 10 mmol) and 1N hydrochloric acid (30 mL) and stir under a nitrogen atmosphere at room temperature for 4 hours. Pour the reaction mixture into ethyl ether and separate the aqueous phase. Wash the aqueous phase with ethyl ether (2×), the neutralize with 5N sodium hydroxide. Evaporate the water in vacuo then purify by ion-exchange chromatography to give the title compound.

Those compounds of Formula Ia–c in which X is represented by a 2-propyne residue are typically made in the following manner. Initially one of the protected compounds according to Formula Ia'–c' is made in which X is represented by hydrogen. This can be done utilizing the methods taught in Reaction Schemes I–IV. The only modification is that X should be represented by hydrogen in the amino compound of structure (4), the amidino compound of structure (6) and the isocyanate of structure (8).

Once the appropriate compound of Formula Ia'–c' has been prepared, it is subjected to an N-alkylation reaction with 1-bromo-2-propyne, (i.e. a compound of the formula, Br—CH$_2$—C≡CH). This N-alkylation can be carried out using techniques well known in the art. Approximately equivalent amounts of the reactants are contacted in an aprotic solvent such as toluene, benzene, or dimethylformamide at a temperature ranging from room temperature to reflux. The reaction is allowed to proceed for a period of time ranging from 1 to 16 hours. The desired product may then be recovered by extraction or concentration. It may then be purified by ion exchange chromatography, preparative C$_{18}$ reverse phase chromatography, or by flash chromatography depending upon the particular protecting group being utilized. This compound may then be subjected to the deprotection and optional functionalizations discussed above in Reactions Schemes I–IV.

The following example is typical of a compounds of formula Ic, wherein W is $CH_2NH_2$, X is 2-propyne, and Z is NH. This example is illustrative only and is not intended to limit the scope of the present invention in any way.

EXAMPLE 14

Preparation of $N^5$-[Imino-(2-propynyl-amino)methyl]-L-ornithine

Step A: $N^2$-t-Butyloxycarbonyl-$N^5$-[Imino-(2-propyneamino)methyl]-ornithine

Mix $N^2$-t-butyloxycarbonyl-L-arginine HCl (3.10 g, 10 mmol), anhydrous potassium carbonate (1.38 g), dimethylformamide (50 mL) and propargyl bromide (1.1 mL). Stir at room temperature to 24 hours. Heat to 60° C. for 8 hours, then heat to 90° C. for 16 hours. Acidify, blow to a residue, apply the residue to a Dowex AG50-X8 column and elute with 0.2M $NH_4OH$ and lyophilize to give the title compound.

Step B: $N^5$-[Imino-(2-propyneamino)methyl]-L-ornithine

Mix $N^2$-t-butyloxycarbonyl-$N^5$-[Imino-(2-propyneamino)methyl]-ornithine (1.44 g, 4.6 mmol) and 10% palladium/carbon (0.5 g) in 95% ethanol (40 mL). Hydrogenate at room temperature at atmospheric pressure. Filter and evaporate the filtrate in vacuo to give the title compound.

As noted above, the compounds of Formula Ia–c inhibit the biosynthesis of nitric oxide and are therefore useful in the treatment of a number of disease states in which excess levels of nitric oxide play a detrimental role. These include conditions associated with low blood pressure, inflammatory diseases and CNS disorders.

As noted above it has been demonstrated that nitric oxide relaxes the smooth muscles of the vasculature, producing a dilatory effect upon these vessels which results in a reduction in blood pressure. Since the compounds of Formula Ia–c inhibit the biosynthesis of nitric oxide, the administration of the compounds of Formula Ia–c will produce a rise in blood pressure and thus can be used to treat conditions associated with low blood pressure. Representative examples of such conditions include shock, endotoxic shock, hypovolemic shock, cardiogenic shock.

In order to exhibit this hypertensive effect it is necessary that the compounds be administered in an amount sufficient to inhibit the biosynthesis of nitric oxide. The dosage range at which these compounds exhibit this hypertensive effect can vary widely depending upon the particular disease being treated, the severity of the patient's disease, the patient, the particular compound being administered, the route of administration, and the presence of other underlying disease states within the patient, etc. Typically the compounds exhibit their hypertensive effects at a dosage range of from about 0.1 mg/kg to 500 mg/kg/day. Repetitive daily administration may be desirable and will vary according to the conditions outlined above. Typically, the compounds will be administered from 1–4 times daily.

The ability of these compounds to inhibit the biosynthesis of nitric oxide can be demonstrated by in vitro assays known in the art. Igengar et al. *Proc. Nat'l. Acad. Sci.*, 84, pages 6369–6373 (September 1987). In this assay macrophages are exposed to bacterial lipopolysaccharides and Interferon-gamma, which stimulates the macrophages to produce nitric oxide. The compounds of Formula Ia–c will either inhibit or decrease production of nitric oxide by the macrophages.

It is well known in the art that excessive activity by macrophages is implicated in a number of inflammatory diseases such as, for example, rheumatoid arthritis, inflammatory bowel disease, multiple sclerosis, cirrhosis of the liver and lungs, sarcoidosis, and granulomatous lesions. In a recent review, Collier et al. stated that it is currently believed that the cytotoxic activity of macrophages is due their ability to produce nitric oxide. *Trends in Pharmacological Sciences*, 10(11), page 123, (1989) Thus the compounds of the instant invention will either inhibit or decrease the amount of nitric oxide which is produced by the macrophages and thus will be useful in the treatment of these disease states associated with excessive activity of macrophages. The compounds will also be useful in preventing transplant rejection by macrophages.

In order to exhibit this beneficial effect in inflammatory diseases, it is necessary that the compounds of Formula Ia–c be administered in a quantity sufficient to inhibit the production of nitric oxide by macrophages. The dosage range at which these compounds exhibit this effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 500 mg/kg/day for any of the diseases or conditions listed above. Repetitive daily administration may be desirable and will vary according to the conditions outlined above.

The ability of these compounds to inhibit the generation of cyclic GMP within the central nervous system can be demonstrated by procedure's known in the art such as Baron et al. *Journal of Pharmacol. and Exp. Therap.*, 250, pages 162–169 (1989). In this test, mice are administered harmaline which produces a rise in cyclic GMP levels with the cerebella of the CNS. The pre-administration of one of the compounds of Formula Ia–c will block the rise in cyclic GMP levels that is typically associated with harmaline administration.

It has been demonstrated that stimulation of the NMDA receptor complex leads to the release of nitric oxide which in turn stimulates guanylate cyclase which in turn produces a rise in cyclic GMP levels. Since the compounds of Formula Ia–c will inhibit the production of cyclic GMP and thus will negate the physiological effects typically associated with stimulation of the NMDA receptor complex, these compounds will be useful in the treatment of disease states associated with overstimulation of these excitatory neurons. Overstimulation of the NMDA receptor complex has been associated with seizures and thus the compounds of Formula Ia–c exhibit anti-convulsant properties and are useful in the treatment of epilepsy. They are useful in the treatment of grand mal seizures, petit mal seizures, psychomotor seizures, and autonomic seizures.

Overstimulation of the NMDA receptor complex has also been associated with the neurotoxicity associated with ischemic, hypoxic, traumatic, or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds of Formula Ia–c are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease or a lack of oxygen or sugar. As used in this application, the term "treat" refers to the ability of the compounds to prevent further damage or delay the rate at which any further damage occurs.

The dosage range at which these compounds will exhibit their effect upon excitatory neurotransmission can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 500 mg/kg/day for any of the diseases or conditions listed above. Repetitive daily administration may be desirable and will vary according to the conditions outlined above.

As used in this application:
a) the term "patient" refers to warm blooded animals such as, for example, guinea pigs, mice, rats, cats, rabbits, dogs, monkeys, chimpanzees, and humans;
b) the term "treat" refers to the ability of the compounds to either relieve, alleviate, or slow the progression of the patient's disease;
c) the term "neurodegeneration" refers to a progressive death and disappearance of a population of nerve cells occurring in a manner characteristic of a particular disease state and leading to brain damage.
d) the term "inflammatory disease" refers to a condition in which activation of leukocytes leads to an impairment of normal physiologic function. Representative examples of such conditions include rheumatoid arthritis, inflammatory bowel disease, sepsis, and adult respiratory distress syndrome.
e) the term "hypotensive condition" refers to a condition in which blood pressure is lowered to a point to which normal physiologic functioning is impaired.

The compounds of the present invention may be administered by a variety of routes. They are effective if administered orally. The compounds may also be administered parenterally (i.e., subcutaneously, intravenously, intramuscularly, intraperitoneally, or intrathecally).

Pharmaceutical compositions can be manufactured utilizing techniques known in the art. Typically an inhibitory amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula Ia–c can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds may also be admixed with any inert carrier and utilized in laboratory assays in order to determine the concentration of the compounds within the serum, urine, etc., of the patient as is known in the art.

What is claimed is:

1. A compound of the formula:

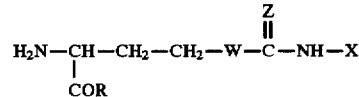

in which
X is represented by cyano, cyclopropyl, 2-propyne, 2,3-butadiene or $NHR_2$, in which $R_2$ is represented by H, or $C_{1-6}$ alkyl;
R is represented by an amino acid or OM in which M is represented by H, $C_{1-6}$ alkyl, benzyl, phenyl, or pivoyl methyl ether;
Z is represented by O or $NR_1$, in which $R_1$ is represented by H, $-CF_3$, $-CH_2CF_3$, or $C_{1-6}$ alkyl; and
W is represented by a substituent selected from the group consisting of $CH_2-NH-$, $-(CH_2)_2-NH-$, $-NH-NH-$, $-CH_2-NH-NH$, $-CH_2-O-NH$ and $-O-NH$;
and the pharmaceutical acceptable salts thereof; with the following proviso's;
1) that when W is $-NH-NH$ or $-(CH_2)_2-NH-$ then Z must be represented by O, and
2) that when X is $-NHR_2$ and Z is $-NHR_1$ then $R_1$ and $R_2$ must t be represented by the same $C_{1-6}$ alkyl substituent, and
3) that when Z is represented by O and X is represented by $NR_1$ then W must be $-CH_2-NH-$ or $-(CH_2)_2-NH-$, and
4) that when W is represented by $CH_2-NH$, Z is represented by NH, and X is $NHR_2$, then $R_2$ is not represented by H.

2. A compound according to claim 1 in which X is cyclopropyl.

3. A Compound according to claim 2 in which R is represented by $-OM$ in which M is represented by H, $C_{1-6}$ alkyl, benzyl, phenyl, pivoyl methyl ester.

4. A Compound according to claim 3 in which R is represented by $-OM$ where M is represented by H.

5. A Compound according to claim 2 in which R is represented by an amino acid.

6. A Compound according to claim 2 in which Z is represented by $NR_1$.

7. A Compound according to claim 2 in which Z is represented by O.

8. A compound according to claim 1 in which W is represented by $-CH_2-NH-$.

9. A compound according to claim 1 in which Z is NR1 where R1 is H.

10. A Compound according to claim 1 in which X is represented by 2-propyne, or 2,3 butadiene.

11. A pharmaceutical composition comprising a compound according to claim 1 in admixture with a pharmaceutically acceptable carrier.

12. A compound of the formula:

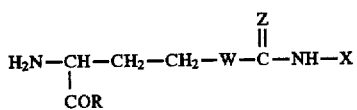

in which

X is cyclopropyl and

R is OM, with M represented by H, and

Z is represented by NR1, with R1 represented by H, and

W is CH2—NH.

13. A pharmaceutical composition consisting of a compound according to claim 12 in admixture with a pharmaceutically acceptable carrier.

* * * * *

UNITED STATES PATENT AND TRADEMARK OFFICE
CERTIFICATE OF CORRECTION

PATENT NO. : 5,710,324

DATED : January 20, 1998

INVENTOR(S) : Jeffrey P. Whitten, Ian A. McDonald, Laurie E. Lambert, Niall S. Doherty It is certified that error appears in the above-identified patent and that said Letters Patent is hereby corrected as shown below:

Column 4, Line 55 of Patent reads "[Imino-(cyclopropylamino)-" and should read –[(cyclopropylamine)- --.

Column 4, Line 63 of Patent reads "8) O-[Hydrazino-carbonyl]-homoserine" and should be deleted.

Column 12, Line 63 of Patent reads "Step A: $N^5$-[Hydrazino-iminomethyl]-2-(acetylamino)-5-amino-3-pentenoic acid" and should read –Step A: 2-Amino-5-[(hydrazino-iminomethyl)amino]-3-pentenoic acid—.

Column 25, Line 21 of Patent reads "(2-propyneamino)" and should read –(2-propynyl-amino) --.

Column 28, Line 35 of Patent reads "$CF_3$,--$CH_2CF_3$" and should be deleted.

Signed and Sealed this

Ninth Day of March, 1999

Attest:

*Attesting Officer*

Q. TODD DICKINSON

*Acting Commissioner of Patents and Trademarks*